United States Patent [19]
DeLuca et al.

[11] Patent Number: 5,160,745
[45] Date of Patent: Nov. 3, 1992

[54] BIODEGRADABLE MICROSPHERES AS A CARRIER FOR MACROMOLECULES

[75] Inventors: Patrick P. DeLuca, Lexington, Ky.; Frantisek Rypacek, Leckova, Czechoslovakia

[73] Assignee: The University of Kentucky Research Foundation, Lexington, Ky.

[21] Appl. No.: 463,008

[22] Filed: Jan. 9, 1990

Related U.S. Application Data

[60] Continuation of Ser. No. 152,843, Feb. 5, 1988, abandoned, which is a division of Ser. No. 864,147, May 16, 1986, Pat. No. 4,741,872.

[51] Int. Cl.$^5$ .................. A61K 9/14; A61K 9/50; A61K 9/52; B01J 13/18
[52] U.S. Cl. .................... 424/487; 424/486; 424/499; 424/501; 428/402.22; 514/2; 514/963; 514/965; 514/885
[58] Field of Search ............ 428/402.22; 424/486, 424/487, 501, 499; 514/963, 2, 885

[56] References Cited

U.S. PATENT DOCUMENTS

| | | | |
|---|---|---|---|
| 3,640,741 | 2/1972 | Etes | 106/170 |
| 3,773,919 | 11/1973 | Boswell et al. | 424/486 |
| 3,786,123 | 1/1974 | Katzen | 264/53 |
| 4,094,833 | 6/1978 | Johansson et al. | 536/51 X |
| 4,178,361 | 12/1979 | Cohen et al. | 424/487 |
| 4,247,406 | 1/1981 | Widder et al. | 424/1.1 X |
| 4,356,166 | 10/1982 | Peterson et al. | 514/2 X |
| 4,451,452 | 5/1984 | Deibig et al. | 514/255 X |
| 4,501,726 | 2/1985 | Schröder et al. | 128/1.3 X |
| 4,741,872 | 5/1988 | DeLuca et al. | 264/4.7 |

OTHER PUBLICATIONS

Ulf Schröder, "Crystallized Carbohydrate Spheres for Slow Release and Targeting", *Methods in Enzymology*, 112, 116 (1985).

Ulf Schröder, "Crystallized Carbohydrate Spheres as a Slow Release Matrix for Biologically Active Substances", *Biomaterials*, 5, 100 (1984).

Fan L. T. et al., "6. Stochastic Model for Diffusion in Porous or Heterogeneous Polymer Matrix", *Controlled Release, A Quantitative Treatment*, Springer-Verlag, New York pp. 167-170 (1989).

Edman et al., "Immobilization of Proteins in Microspheres of Biodegradable Polyacryldextran", *Journal of Pharmaceutical Sciences*, vol. 69, No. 7, Jul. 1980, pp. 838-842, American Pharmaceutical Association.

*Primary Examiner*—Richard D. Lovering
*Attorney, Agent, or Firm*—Burns, Doane, Swecker

[57] ABSTRACT

A method for preparing biodegradable microspheres having a three-dimensional network in which biologically active macromolecular agents are physically entrapped therein. The microsphere is able to degrade and release the macromolecular agent at a controlled rate. The method involves emulsifying a vinyl derivative of a biodegradable hydrophilic polymer, a water-soluble monovinyl monomer and a biologically active macromolecule in water, and copolymerizing the biodegradable hydrophilic polymer and the water-soluble monovinyl monomer such that the biologically active macromolecule is entrapped therein.

13 Claims, 2 Drawing Sheets

BIODEGRADABLE MICROSPHERES AS A CARRIER FOR MACROMOLECULES

This application is a continuation of application Ser. No. 07/152,843, filed Feb. 5, 1988, now abandoned, which is a divisional of application Ser. No. 06/864,147, filed May 16, 1986, now U.S. Pat. No. 4,741,872.

BACKGROUND OF THE INVENTION (1) Field of the Invention

The present invention relates generally to the field of biodegradable polymers for the controlled release of biologically active agents therefrom. More particularly, the present invention relates to a process for preparing biodegradable polymers in the form of spherical particles of controlled size. The process is designed to allow the biodegradable polymer particles to contain incorporated biologically active agents and to allow controlled release of these agents while allowing targeted delivery via injection or inhalation.

(2) Background of the Prior Art

The use of proteins and peptides as therapeutic agents has been recognized and their position within the pharmaceutical armamentarium is growing due to their increasing availability. This availability is primarily due to recent advances in genetic engineering and biotechnology. Unfortunately, the use of proteinaceous drugs by conventional routes of administration is generally hampered by a variety of delivery problems. Nonparenteral routes of administration, i.e., oral and percutaneous, are inefficient primarily due to poor absorption of proteinaceous drugs into the bloodstream and degradation of such drugs in the gastrointestinal tract. Rapid proteolytic inactivation of the proteinaceous drug also occurs when the drug is administered parenterally thus decreasing its bioavailability. In addition, when administered by the parenteral route, the host's immune system is activated thereby potentially setting off a series of undesirable immune reactions.

In view of the foregoing, considerable effort has been devoted to developing alternative systems for parenteral delivery of peptides and proteins to obviate the problems associated with prior art administration techniques. For instance, implantable devices have been cast or molded from poly-(hydroxyethyl)methacrylate, polyvinyl alcohol, ethylene-vinylacetate copolymer (EVA) and silicone elastomer. Macromolecular drugs have been embedded in those devices. A typical method of preparation involves suspending a powder of a macromolecular drug such as a solid protein or peptide in a solution containing the polymer. The entire composition is then cast or molded into the desired size and shape either by evaporating the solvent or by vulcanization. A sustained release of macromolecules from these devices has been demonstrated. The simplicity of the foregoing prior art method is its primary advantage.

However, one disadvantage of hydrophobic polymers such as those prepared from EVA and silicon, is that those polymers are not permeable to hydrophilic macromolecules, thus, only that portion of the drug which communicates with the surface of the implant, either directly or via contact with other drug particles, can be released. Thus, the drug present nearer the interior of the implant and completely surrounded by the polymer matrix is unable to ever be released and never exerts its therapeutic effect. Addition of polar additives increases penetration of water in these hydrophobic materials and helps to dissolve the protein, but they are not quite inert to the protein, as are the polar organic solvents used for casting from PHEMA and PVA. Another disadvantage associated with these types of devices is the need for surgical insertion and eventually surgical removal of the implant. This is necessary since the devices are composed of materials which are nondegradable.

Microspheres containing proteins have been prepared from polyacrylamide, acryloylated dextran and acryloylated starch. Polyacrylamide beads can meet different purposes in vitro, but their nondegradability prevents their use in humans. Reported data on polysaccharide particles show that an efficient crosslinking has been achieved only at a high degree of derivatization (D.D. about 0.1 to 0.3). A high D.D. is disadvantageous as it decreases the biocompatibility of the polymer. A high D.D. also leads preferentially to the intramolecular reaction of polymerizable groups instead of the intermolecular reaction between different polymer chains, which results in a heterogenous microporous structure. The use of the crosslinking agent bisacrylamide is not considered desirable, since it generally results in the formation of crosslinked hydrocarbon gels, which neither dissolve nor degrade even after degradation of the polysaccharide component.

The recent advances in the incorporation of drugs into microparticulate carriers has attracted a great deal of attention because it combines features of matrix-controlled release with those of injectable forms. In addition to controlled release, these microspherical carriers offer "first stage" physical targeting, that is, physical localization of the drug carrier in the proximity of the target tissue and cells. Localized administration of the therapeutic agent allows for not only more efficient drug therapy but also minimizes the opportunity for adverse systemic effects.

In preparing microspheres in the size range of 1 $\mu$m to 20 $\mu$m, homogenous systems are more suitable than heterogenous systems for casting implants. In the homogenous system, proteins are co-dissolved in the same solvent as the material of the matrix. Furthermore, in order to preserve the biological activity of the macromolecules, aqueous systems are generally preferred. In this regard, biodegradable hydrophilic polymers can be chosen as matrix material provided that they can be solidified or crosslinked by a mechanism which does not involve a chemical modification and/or denaturation of the incorporated macromolecule such as a proteinaceous agent.

It is known that crosslinked hydrophilic gels can be obtained utilizing techniques of free-radical polymerization. To some extent, the problems identified above are similar to those found in the preparation of graft biodegradable polymers, that is, polymers containing vinylic groups with the encapsulation of biologically active materials therein.

Examples of prior art patents include U.S. Pat. Nos. 4,131,576, 3,687,878, 3,630,955 and 3,950,282. These patents disclose methods for the preparation of graft copolymers of polysaccharides and vinylic monomers. These patents were directed to improving the physical properties of the polysaccharides within each composition. Process conditions used to achieve these improvements included the use of elevated temperatures, highly reactive monomers or organic solvents. However, each of the foregoing parameters are harmful to biologically active macromolecules and thus are unsuitable in the practice of the present invention.

The prior art also discloses procedures for encapsulation of a core material in a polymer capsule. U.S. Pat. No. 4,382,813 discloses the production of a capsule wall by the gelation of polysaccharide gums, such as alkali-metal alginates, with bivalent metal cations. U.S. Pat. No. 4,344,857 discloses the gelation of xanthates of polyhydroxy polymers by the addition of strong acids and coupling agents. U.S. Pat. No. 3,567,650 achieves a similar result by lessening the solubility of certain polymeric materials using increasing temperature.

Other mechanisms are based on the principle of complex coacervation using at least two colloids of opposite electrical charge and oxidation products of polysaccharides as crosslinking agents as disclosed in U.S. Pat. No. 4,016,098. Yet another procedure employs interfacial crosslinking of the wall-forming polymer by reactive bifunctional crosslinking agents dissolved in oil droplets which are encapsulated as taught in U.S. Pat. No. 4,308,165. Other examples of the prior art which offer similar teachings include U.S. Pat. Nos. 4,078,051, 4,080,439, 4,025,455 and 4,273,672. Materials which are encapsulated according to the prior art are mostly water insoluble solids or oil droplets and compounds dissolved therein, e.g., dyes, pigments or biologically active low-molecular-weight compounds like herbicides.

U.S. Pat. No. 4,352,883 teaches a method for encapsulation of core materials such as living tissues or individual cells in a semipermeable membrane. The membrane is permeable for small molecules but not permeable to large molecules. This patent also utilizes the gelation of certain water-soluble gums by the action of multivalent cations.

U.S. Pat. No. 4,038,140 discloses the procedure for binding of biologically active proteins onto an insoluble carrier by reacting the proteins in an aqueous phase with a carrier comprising an activated polysaccharide having a hydrophilic graft copolymer incorporated therein. That patent is directed to the preparation of insoluble carriers containing covalently bound proteins with application in biochemical reactors.

Yet another example of the prior art, U.S. Pat. No. 4,094,833, teaches a procedure for preparation of copolymerizates of vinylic group containing dextran and divinyl compounds, optionally also monovinyl compounds, in the form of three-dimensional gel networks. The resulting crosslinked dextran-vinylic gels can be used for separation purposes.

In spite of the numerous teachings of the prior art, the prior art does not offer a method for obtaining encapsulated or entrapped biologically active macromolecules such as proteinaceous agents in spherical microparticles of controlled size ranges. Nor does the prior art suggest a procedure for allowing microspheres to have the potential to control the rate by which the biologically active macromolecule is released or for modulating the rate by which the matrix is degraded in vivo.

SUMMARY OF THE INVENTION

It is, therefore, the object of this invention to provide a process for the incorporation of sensitive biologically active macromolecules, preferably peptides and proteins, into a biodegradable and biocompatible matrix under conditions sufficiently mild to retain the biological activity of the incorporated macromolecular agents.

It is another object of this invention to provide for a matrix, containing pharmacologically active macromolecules, in the form of spherical particles of controlled size, preferably having a diameter in the range of about 0.5 $\mu$m to about 500 $\mu$m.

It is also an object of this invention to produce microspherical carriers from which macromolecular agents are released under in-vivo conditions at a predictable rate.

It is yet another object of this invention to produce microspherical carriers of biologically active macromolecules which possess a potential for controlling the rate of biodegradation of the matrix so that the release of the macromolecular agents can be regulated by the biodegradation of the matrix.

A further object of the present invention is to produce microspherical carriers of biologically active macromolecules which possess a potential for controlling the rate of biodegradation of the matrix by adjusting the matrix properties thereby controlling both release of the macromolecular agent and existence of the matrix in the tissue as well as assuring the biodegradation of the matrix into nontoxic soluble products which are metabolized and/or excreted.

A still further object of the present invention is to provide a microspherical drug delivery system which allows targeting of drugs or other agents to specific host tissues or cells via injection or inhalation providing high localized concentrations, sustained activity, systemic administration and treatment, thereby minimizing undesirable systemic effects of toxic drugs administered directly into the circulation.

These and similar objects, advantages and features are accomplished according to the methods and compositions of the following description of the present invention.

DESCRIPTION OF THE PREFERRED EMBODIMENTS

Figure 1:
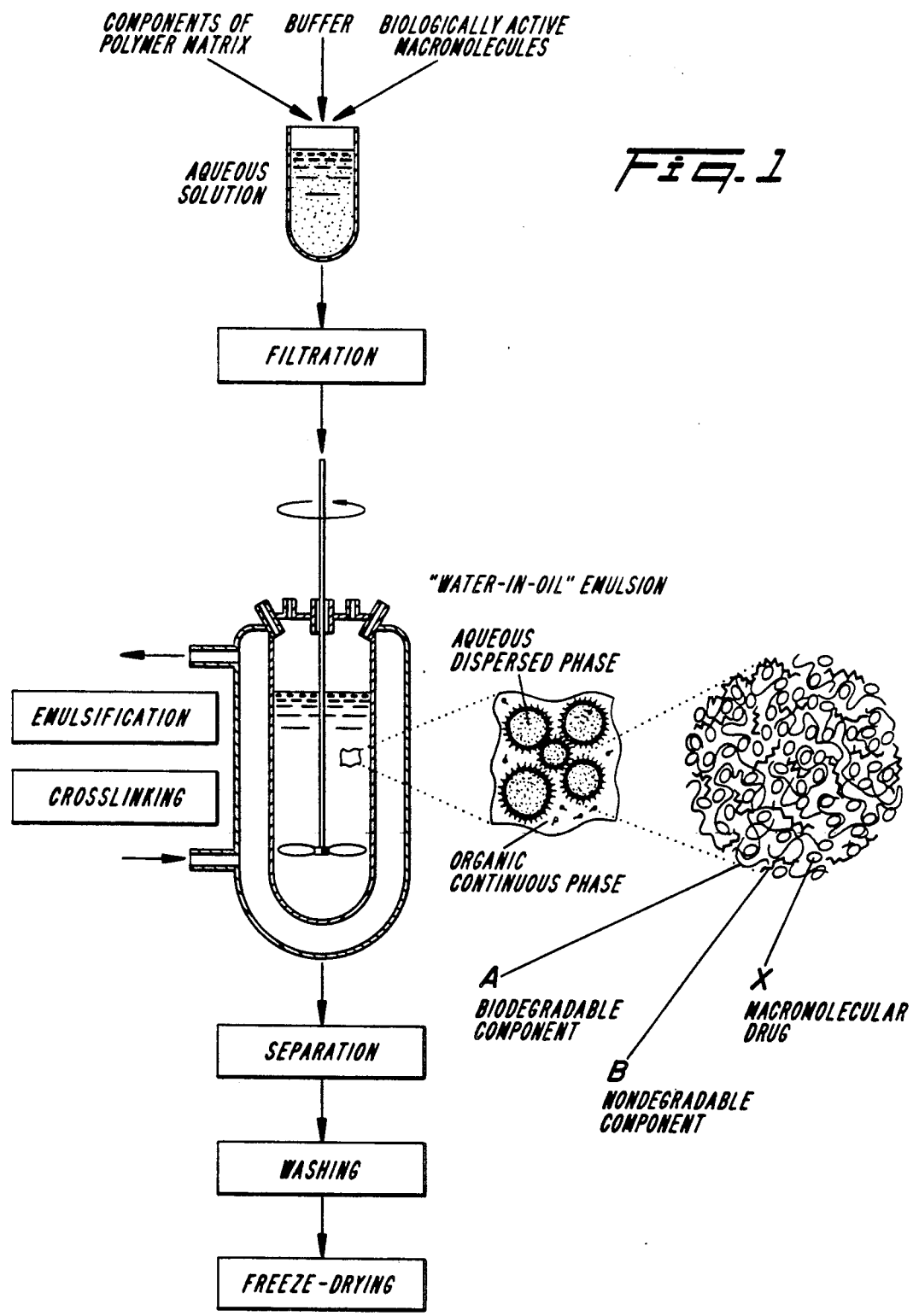
FIG. 1 depicts an overall scheme for preparation of the biodegradable microspheres of the present invention.

The present invention provides a process for the incorporation of sensitive biologically active macromolecules into a biodegradable matrix. The biodegradable matrix is prepared by the copolymerization of a vinyl derivative of biodegradable hydrophilic polymer containing at least two vinyl groups per polymer chain with a monovinyl water-soluble monomer. The biodegradable matrix is a three-dimensional gel network in which biologically active macromolecules are physically entrapped. The biodegradable matrix is particularly well-suited for the parenteral route of administration.

According to the present invention, the biodegradable hydrophilic polymer component of the matrix can be selected from a variety of sources including polysaccharides, proteinaceous polymers, soluble derivatives of polysaccharides, soluble derivatives of proteinaceous polymers, polypeptides, polyesters, polyorthoesters, and the like.

The polysaccharides may be poly-1,4-glucans, e.g., starch glycogen, amylose and amylopectin, and the like. Preferably, the biodegradable hydrophilic polymer is a water-soluble derivative of a poly-1,4-glucan, including hydrolyzed amylopectin, hydroxyalkyl derivatives of hydrolyzed amylopectin such as hydroxyethyl starch (HES), hydroxyethyl amylase, dialdehyde starch, and the like.

Proteinaceous polymers and their soluble derivatives include gelation biodegradable synthetic polypeptides, elastin, alkylated collagen, alkylated elastin, and the like.

Biodegradable synthetic polypeptides include poly-(N-hydroxyalkyl)-L-asparagine, poly-(N-hydroxyalkyl)-L-glutamine, copolymers of N-hydroxyalkyl-L-asparagine and N-hydroxyalkyl-L-glutamine with other amino acids. Suggested amino acids include L-alanine, L-lysine, L-phenylalanine, L-leucine, L-valine, L-tyrosine, and the like.

Definitions or further description of any of the foregoing terminology are well known in the art and may be found by referring to any standard biochemistry reference text such as "Biochemistry" by Albert L. Lehninger, Worth Publishers, Inc. and "Biochemistry" by Lubert Stryer, W. H. Freeman and Company, both of which are hereby incorporated by reference.

The aforementioned biodegradable hydrophilic polymers are particularly suited for the methods and compositions of the present invention by reason of their characteristically low human toxicity and virtually complete biodegradability. Of course, it will be understood that the particular polymer utilized is not critical and a variety of biodegradable hydrophilic polymers may be utilized as a consequence of the novel processing methods of the invention.

The three dimensional network or gel matrix according to the present invention is obtained by the free-radical polymerization of the biodegradable hydrophilic polymer containing at least two vinyl or substituted vinyl groups with an additional monovinylic monomer.

The vinyl derivatives of the biodegradable hydrophilic polymer include derivatives containing groups of the formula (I):

$$CH_2=CR_1-(CH_2)_n-X \qquad (I)$$

wherein $R_1$ is a hydrogen atom or methyl group; n is 0, 1 or 2; and X is a radical having the formula

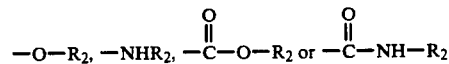

$$-O-R_2, \quad -NHR_2, \quad -\overset{O}{\underset{\|}{C}}-O-R_2 \text{ or } -\overset{O}{\underset{\|}{C}}-NH-R_2$$

wherein $R_2$ represents the above-mentioned biodegradable polymer which contains at least two vinyl or substituted vinyl groups per average polymer chain. Thus, X represents an ether, secondary amine, ester or amide bridge between the group of formula (I) and the biodegradable hydrophilic polymer. Therefore, typical examples of vinyl substituents include vinyl, allyl, acryloyl, methacryloyl, acrylamido and methacrylamido groups.

The vinyl derivatives of the biodegradable hydrophilic polymer can be prepared in a variety of ways well known in the prior art. One suggested approach is the preparation of vinyl and allyl ethers by the reaction of vinyl alkylhalides, allylhalides, vinylglycidyl ethers or allylglycidyl ethers with alkaline solutions of the selected biodegradable hydrophilic polymer containing either hydroxyl or amino groups. In a like manner, derivatives containing either ester or amide linkages can be prepared by reacting acryloyl chlorides, methacryloyl chlorides, acryloyl glycidyl esters or methacryloyl glycidyl esters with hydroxyl or amino groups of the biodegradable hydrophilic polymer.

The degree of derivatization (DD) of the biodegradable hydrophilic polymer by the vinyl groups is such, that they are at least two vinyl groups per average polymer chain, preferably, at least three vinyl groups per average polymer chain. The upper limit of DD is given by the desired density of crosslinking as discussed below. It should also be noted that the minimum DD, when expressed in moles of vinyl groups per mole of monomer units of biodegradable hydrophilic polymer also depends on the molecular weight of the biodegradable hydrophilic polymer.

The monovinyl monomer has two functions. First, it is intended to facilitate the propagation reaction of the growing radical by lessening steric hindrance during the polymerization of the macromolecular vinyl derivatives. This obviates the necessity of a high degree of derivatization of the starting biodegradable hydrophilic polymer. And second, it is intended to introduce into the gel structure or matrix a nondegradable component which can participate in the regulation of the degradation rate of the matrix.

The ratio of the monofunctional monomer propagator to derivatized biodegradable hydrophilic polymer is chosen such, that during the polymerization, short linear chains of hydrocarbon polymers are produced which are in fact crosslinked by degradable hydrophilic polymer chains. This assures that substantially the entire matrix of microspheres can be degraded in vivo to low molecular weight soluble products.

The ratio between the biodegradable hydrophilic polymer component to the vinyl monomer component may be in the range of about 1:5 up to about 40:1 based on a weight basis. Preferably, the ratio is in the range of about 2:1 to about 20:1.

The monovinyl monomer is designed to facilitate the propagation reaction of the growing radical during polymerization thereby obviating the necessity of high derivatization of starting polysaccharide with polymerizable groups. The monovinyl monomer also introduces in the polymer matrix other functional groups, e.g., negatively or positively charged, which can participate in the control of drug release. Typical functional groups which may participate in the control of drug release include carboxyl, amino, dialkylamino, dihydroxyalkylamino, and the like. The presence of these positive or negative charges provide ion-exchange properties to the matrix.

The monovinyl monomer may be selected from the group of hydrophilic esters and/or amides of acrylic or methacrylic acids, water-soluble vinyl derivatives, acrylic acid, methacrylic acid, and the like. Typical examples of hydrophilic esters and/or amides of acrylic or methacrylic acids include acrylamide, methacrylamide, 2-hydroxyethyl methacrylate, 2-hydroxypropyl methacrylamide, N-methylacryloyl-trishydroxymethylaminomethane, N-acryloyl-N'-dimethylaminopropylamine, 3-N,N-dimethylaminopropylmethacrylamide, N-alkylmethacrylamide glyceryl monomethacrylate, and the like. Suitable water-soluble vinyl derivatives include N-vinylpyrrolidone, N-vinylimidazole, p-vinylbenzoic acid, vinylpyridine, and the like.

Suitable biologically active macromolecules intended to be used in the practice of the present invention include hormones, proteins, peptides, vaccines, enzymes, enzyme inhibitors and other biologically active macromolecules. A suggested inhibitor is alpha-1-antitrypsin (ATT), an $\alpha$-proteinase inhibitor. Additional examples include amino acid metabolizing enzymes in the treatment of neoplasia, fibrinolytic enzymes, interferon, growth hormone, antigens for desensitization, immunoglobulins and $F_{ab}$-fragments of immunoglobulins. The present invention is not intended to be limited to any of the foregoing and other types of biologically active macromolecules are equally suitable in the practice of the present invention.

The biologically active macromolecules remain free within the polymer matrix, that is, there are no chemical bonds between the macromolecule or some other group within the microsphere. Thus, the macromolecule does not require the breakage of a chemical bond to be released. Release occurs through diffusion out of the microsphere or biodegradable erosion of the polymer.

The polymerization reaction according to the present invention is conducted under suitable conditions for free radical polymerization. The reaction is always conducted in aqueous solution. Suitable free radical initiators are redox type initiators. The polymerization reaction is preferably conducted using free radical initiators to produce free radicals under mild conditions such as a temperature of approximately 0° C. However, the temperature of the polymerization reaction may range from about 0° C. to about 50° C. The preferred temperature at which to conduct the polymerization reaction ranges from about 0° C. to about 30° C.

It is a particularly advantageous feature of the present manufacturing procedure that, starting from the dissolution of the macromolecule of interest until dispensing the final microspheres in vials, the entire process can be carried out at temperatures near 0° C. in order to minimize the denaturation effect on the macromolecule. Typical redox type initiators include ammonium persulfate, hydrogen peroxide, benzoyl peroxide, and the like.

It is also advantageous to use a free radical initiator along with a compound which forms with the initiator a redox system and accelerates the formation of radicals. Examples of the second compound of the initiator system include N,N,N'N'-tetramethylethylenediamine, ascorbic acid, N,N-dimethylamino-p-toluidine, 3-dimethylaminopropionitrile, sodium metabisulfite, and the like.

During the polymerization reaction, linear chains of vinylic polymer are formed which are cross-linked with the biodegradable hydrophilic polymer. It is thus important that a monovinyl monomer is used during the polymerization reaction to ensure that only linear chains of nondegradable hydrocarbon polymers are formed. Thus, the use of the monovinyl monomer ensures that the degradation of the biodegradable component which is responsible for the crosslinking will allow for the formation of totally soluble degradation products. The monovinyl monomer of the present invention, since it is only a monomer, will have a low molecular weight compared to the biodegradable polymer. It has been speculated that if the molecular weight of the monomer exceeds 400, then steric hindrance is possible. Thus, it is recommended for purposes of the present invention that the monovinyl monomer have a molecular weight of less than 400.

The drug delivery system in accordance with the present invention is ideally suited for administration by parenteral or inhalation routes. It will be appreciated by those skilled in the art that the porous microspheres of the present invention containing incorporated drugs for release to target cells or tissues, therefore, may be administered alone or in admixture with appropriate pharmaceutical diluents, carriers, excipients or adjuvants suitably selected with respect to the intended route of administration and conventional pharmaceutical practices. These inert pharmaceutically acceptable adjuvants are well known in the art. For example, for parenteral injection, dosage unit forms may be utilized to accomplish intravenous, intramuscular or subcutaneous administration, and for such parenteral administration, suitable sterile aqueous or non-aqueous solutions or suspensions, optionally containing appropriate solutes to effect isotonicity, will be employed. Likewise for inhalation dosage forms, for administration through the mucous membranes of the nose and throat or bronchiopulmonary tissues, suitable aerosol or spray inhalation compositions and devices will be utilized.

The foregoing methodology allows for the preparation of microspheres in controlled size ranges under conditions sufficiently mild to preserve the biological activity of functional macromolecules. In addition, the foregoing methodology allows for the potential for controlling the release of the drug by controlling the crosslinking density and the rate of degradation via selecting the derivatization degree of the starting polysaccharide and matrix composition.

The polymerization may be conducted by any polymerization process known in the art, however, another important feature of the present invention is the fact that the polymerization can be conducted using a bead polymerization technique. According to the convenient process described in the present invention, the derivatized biodegradable hydrophilic polymer, the monovinyl monomer and the biologically active macromolecule which is to be incorporated therein are codissolved in an aqueous buffer of appropriate pH and ionic strength which is suitable for preserving the biological activity of the macromolecular agent, usually together with one component of the initiator system. Either oxidative or reductive types of initiators are useful.

The aqueous solution is then deoxygenated by purging with $N_2$ and emulsified in a deoxygenated water-immiscible organic liquid, preferentially composed of higher aliphatic hydrocarbons such as hexane, heptane, octane, cyclohexane, or their higher homologs and their mixtures. In order to facilitate the emulsification and formation of a water-in-oil emulsion, appropriate emulsifying agents are added to the continuous organic phase. Typical emulsifying agents include sorbitan oleates, polyethylene glycol ethers, polyoxyethylene sorbitan esters, polyoxyethylene polyoxypropylene alcohols, and the like.

After obtaining an emulsion having a suitable size range of aqueous droplets, the polymerization is begun by addition of the other component of the initiator system to the emulsion. When a water soluble compound is used, the oxidant component of the initiator system, e.g., ammonium persulfate and the like, is in the aqueous dispersed phase, then the second component is a reductant soluble in the continuous phase, e.g., N,N,N',N'-tetramethylethylenediamine and the like.

The microspheres formed by the polymerization of the aqueous droplets of the emulsion are cleansed by decantation and washed with an appropriate water-immiscible organic solvent and then freeze dried. Suitable organic water-immiscible solvents include cyclohexane, benzene, cyclohexanone, and the like.

Following another procedure according to the present invention, the microspheres after washing with organic solvent can be redispersed in water or an aqueous buffer, washed with the buffer and freeze-dried from an aqueous suspension. The biologically active compound, e.g., peptide, protein, and the like, while co-dissolved in the aqueous dispersed phase, is entrapped in the crosslinked polymer network during polymerization and can be released in vivo essentially by the diffusion through the polymer network or following the degradation of the matrix.

A particularly advantageous feature of the foregoing process, and irrespective of the particular polymerization technique selected, is that the microspheres can be prepared in a variety of size ranges generally ranging from about 0.5 $\mu$m to about 500 $\mu$m in diameter. Size ranges from about 1.0 $\mu$m to about 15.0 $\mu$m in diameter are generally preferred. For inhalation administration a microsphere size range of from about 1.0 $\mu$m to about 5.0 $\mu$m in diameter is preferred. For injectable administration a microsphere size range of about 8.0 $\mu$m to about 15.0 $\mu$m in diameter is preferred.

The size of the resulting microspheres depends on the size of the aqueous droplets in the water-in-oil emulsion. The size of the droplets in turn is dependent upon the shear stress which is applied by the stirrer. The stirrer opposes the coalescing tendencies caused by surface tension. Generally, the size of the droplets is reduced by applying a higher shear stress. A higher shear stress is achieved either by using a higher stirrer speed or by increasing the ratio between the viscosities of the continuous phase and the dispersed phase. A higher viscosity of the continuous phase may be achieved by increasing the proportion of hydrocarbons with more carbon atoms in the emulsion, e.g., octane, dioxane, dodecane and the like. The viscosity of the aqueous dispersed phase may be adjusted by using a different molecular weight of the starting biodegradable hydrophilic polymer. Adjustment of the viscosity of the aqueous dispersed phase in this manner allows for use of the same total gel matrix and monovinyl monomer concentration.

Another advantageous feature of the present invention is the fact that the incorporated macromolecular agents are released from the gel matrix by a diffusion through the crosslinked hydrogel network. Various rates of release of the macromolecular agents may be achieved by varying the crosslinking density of the gel matrix. The crosslinking density of the matrix may be varied by selecting a biodegradable hydrophilic polymer with varying degrees of derivatization (DD). Degrees of derivatization are used to indicate the average distance between the attached vinylic groups. A suitable crosslinking density is also dependent on the molecular weight of the macromolecular agent and on the desired rate of its release.

The degree of derivatization is preferably in the range of about 0.01 to about 0.20 mole of vinyl groups per mole of monomer units of the biodegradable hydrophilic starting polymer. Preferably, there are about 0.02 to about 0.15 mole of vinyl groups per mole of monomer units of the starting polymer. If hydroxyethyl starch (HES) is used as the starting biodegradable hydrophilic polymer, the broad range of about 0.01 to about 0.20 corresponds to a molecular weight of the average segment between crosslinking points of about 20,000 to about 1000, respectively. About 0.02 to about 0.15 corresponds to a molecular weight range of the average segment between the crosslinking points of about 10,000 to about 1,800. The range in cross-linking density of 0.02 to 0.15 moles of vinyl groups per moles of monomer units will produce approximately a ten-fold difference in the release rate of the protein having a molecular weight of about 50,000.

It will be appreciated that the concentrations, temperatures and ratios referred to hereinabove and in the examples set forth operable ranges and that other numerical expressions may apply as different solvents, polymers, monomers, macromolecules, etc. are selected.

The following non-limiting examples are offered in order that those skilled in the art may more readily understand the present invention and the specific preferred embodiments thereof. Unless indicated otherwise, all amounts are given in grams.

EXAMPLE 1

To a solution of hydroxyethyl starch (HES) (HES-PAN, a trademark of American Critical Care) in dry, distilled N,N'-dimethylacetamide (DMAA) at approximately 0° C., a measured amount of distilled acryloyl chloride was added in small portions along with an equimolar amount of triethylamine, over approximately a 30 minute time period. The reaction vessel was maintained at this temperature and the reaction proceeded for approximately 2 additional hours. The reaction mixture was then transferred to a vessel containing 200 ml of acetone at about 0° C. to about 5° C. to precipitate the polymer. The polymer was washed with acetone, dried with air suction, dissolved in water and reprecipitated in acetone. Derivatized HES (acryloyl-HES) was finally purified by preparative gel permeation chromatography in water and then freezedried. Ratios of the reactants and the data on the resulting polymers are presented in Table 1. The symbol $mw_A$ represents the molecular weight equivalent of the biodegradable hydrophilic polymer per vinyl group. D.D. represents the degree of derivatization in millimole/gram.

TABLE I

| Preparation of Acryloyl-HES | | | | |
|---|---|---|---|---|
| | 1a | 1b | 1c | 1d |
| HES | 5.0 | 5.0 | 5.0 | 5.0 |
| DMAA | 18.8 | 18.8 | 18.8 | 18.8 |
| Acryloyl chloride | 0.1 | 0.2 | 0.4 | 1.0 |
| Triethylamine | 0.11 | 0.22 | 0.45 | 1.1 |
| Acryloyl-HES (yield) | 4.3 | 4.3 | 4.6 | 5.1 |
| D.D. (mmole/gram) | 0.07 | 0.17 | 0.26 | 0.62 |
| $mw_A$ | 14,300 | 6,000 | 3,800 | 1,600 |

EXAMPLE 2

Approximately 4.05 grams of partially hydrolyzed amylopectin was dissolved in 80 ml of water. The solution was cooled to 0° C. and the solution of 1.8 grams of acryloyl chloride in 10 ml of acetone was added in small portions during stirring along with 10 ml of 2 N solution of NaOH so that the solution was remained alkaline. After approximately 30 minutes the acryloyl-amylopectin was precipitated with acetone and further processed in a manner similar to Example 1. The yield was 3.9 grams and the D.D. was 0.32 mmole/gram.

EXAMPLE 3

Approximately 5.0 grams of HES was dissolved in 18.8 grams of DMAA and to this solution was added 6 ml of 2N solution of NaOH, 50 mg of 4-methoxyphenol and 1.4 grams of allylglycidyl ether. The resulting mixture was stirred for 20 hours at room temperature and then processed in a manner similar to Example 1. The yield was 4.3 grams and the D.D. was 0.42 mmole/gram.

EXAMPLE 4

Approximately 4.3 grams of poly-[N-(2-hydroxyethyl)-L-glutamine], (PHEG), in 18.8 grams of DMAA was reacted with 0.4 grams of acryloyl chloride in a procedure similar to that used in Example 1. The yield of acryloyl-PHEG was 4.2 grams and the D.D. was 0.32 mmole/gram.

EXAMPLE 5

Acryloyl-HES, prepared according to Example 1, acrylamide and alpha-1-proteinase inhibitor (alpha-1-PI) were dissolved in 0.05 mole/liter ammonium carbonate buffer pH 7.4, together with ammonium persulphate (2% mole/mole in terms of the total concentration of vinyl groups). The solution was deoxygenated by repeated evacuation and filling of the vessel with nitrogen at 0° C. The deoxygenated solution was filtered and the filtrate was transferred to a polymerization reactor containing 60 ml of organic continuous phase. The organic continuous phase was composed of a mixture of heptane, USP, mineral oil and 0.3 gram of SO-15 (sorbitan oleate). The entire mixture was then flushed with nitrogen at 0° C. Table II provides a description of the compositions of the dispersed and continuous phases. In Table II, average diameter ($\mu$m) represents the average diameter of the microspheres after rehydration in 0.15 mole/liter NaCl and 0.05 mole/liter phosphate pH 7.4. The protein content % represents the content of the diffusion releasable protein in dry microspheres.

The polymerization reactor consisted of a jacketed glass vessel equipped with a controlled-speed stirrer. Ports for addition of reactants and withdrawal of samples as well as nitrogen inlet were provided in the vessel-top assembly. When a stable emulsion of the aqueous dispersed phase in the organic continuous phase was obtained by the action of the stirrer, approximately 0.15 ml of N,N,N',N'-tetramethylenediamine (TEMED) was added to the emulsion and the reaction proceeded at about 0° to 2° C. for another 20 minutes. The resulting suspension of microspheres was poured in 200 ml of cold heptane (0°–5° C.), washed with heptane, resuspended in ammonium carbonate buffer containing 0.1% of Triton-X-100, washed with pure ammonium carbonate buffer (0.01 mole/liter) and freezedried.

TABLE II

| | Reaction conditions and characteristics of the product | | | | | | | |
|---|---|---|---|---|---|---|---|---|
| | a | b | c | d | e | f | g | h |
| Dispersed phase: | | | | | | | | |
| Acryloyl-HES | 1.76 | 1.76 | 1.76 | 2.00 | 2.00 | 2.00 | 2.00 | 2.00 |
| Acrylamide | 0.40 | 0.40 | 0.40 | 0.50 | 0.50 | 0.50 | 0.50 | 0.50 |
| Alpha-1-PI | 0.34 | 0.34 | 2.20 | 0.60 | 0.60 | 0.60 | 0.60 | 0.60 |
| Buffer | 17.50 | 17.50 | 15.60 | 16.90 | 16.90 | 16.90 | 16.90 | 16.90 |
| $mw_A$ | 3,800 | 6,000 | 3,800 | 3,800 | 6,000 | 6,000 | 6,000 | 6,000 |
| Continuous phase: | | | | | | | | |
| Heptane (ml) | 17 | 17 | 17 | 17 | 17 | 17 | 40 | 10 |
| Mineral oil (ml) | 43 | 43 | 43 | 43 | 43 | 43 | 20 | 50 |
| Stirring (rpm) | 1,600 | 1,600 | 1,600 | 1,600 | 800 | 2,200 | 2,200 | 2,200 |
| Average diameter ($\mu$m) | 8.6 | 14.0 | 12.5 | 7.6 | 28.0 | 5.8 | 46.0 | 3.6 |
| Protein content % | 4.7 | 4.5 | 22.8 | 9.4 | — | — | — | — |

EXAMPLE 6

Example 6 was conducted in a manner similar to Example 5, except that the product was washed with heptane, then washed with cyclohexane and finally freeze-dried from cyclohexane. The resulting microspheres exhibited properties analogous to those found in Example 5 but contained essentially all of the protein which had been initially added in the dispersed phase.

EXAMPLE 7

Approximately 1.6 grams of acryloyl-PHEG, prepared according to Example 4, 0.58 gram of N-vinyl-2-pyrrolidone and 0.49 gram of alpha-1-proteinase inhibitor (alpha-1-PI) in 13.5 ml of 0.05 mole/liter phosphate buffer pH 7.4 were used as a dispersed phase to prepare microspheres in a manner similar to that set forth in Example 5d. The resulting microspheres had an average diameter of 6.7 $\mu$m and a protein content of 11.2%.

EXAMPLE 8

Figure 2:
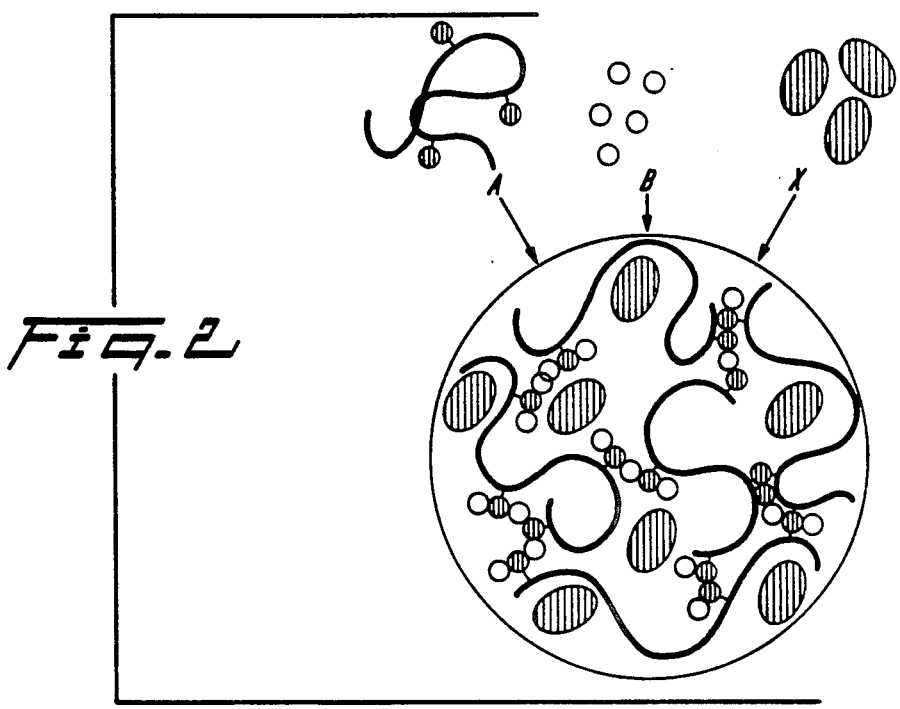
FIG. 2 represents a more detailed view of the microsphere prepared by the process depicted in FIG. 1.
Figure 3:
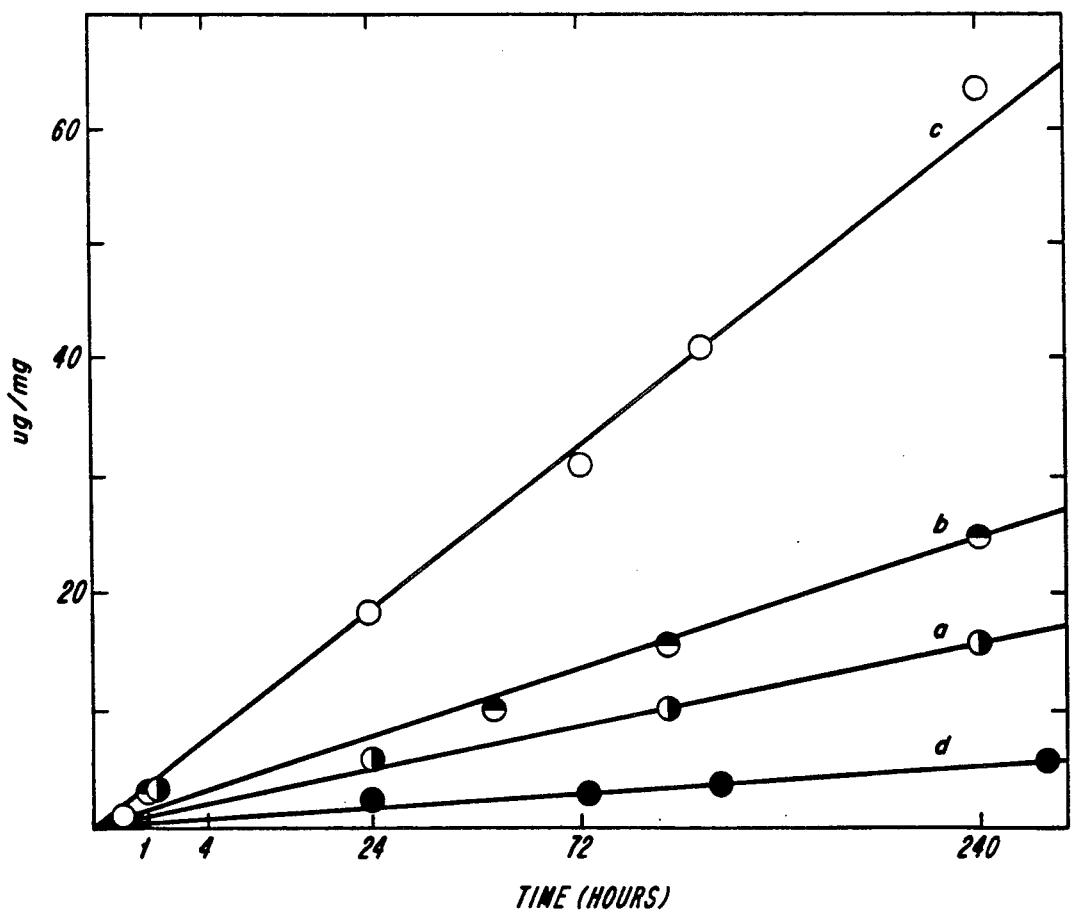
FIG. 3 depicts the cumulative release of alpha-1-proteinase inhibitor from hydroxyethyl starchpolyacrylamide microspheres in $\mu$g of protein per mg of microspheres.

Approximately 50 mg of microspheres prepared in a manner similar to that used in Examples 5a–d were suspended in 10 ml 0.05 mole/liter phosphate buffer pH 7.4 with 0.15 mole/liter NaCl and 0.02% $NaN_3$. The suspensions were placed in capped test tubes and were incubated at 37° C. with continuous agitation. Samples of the suspensions were withdrawn at convenient intervals and the microspheres were separated by centrifugation. The residual amount of the protein in the microspheres, the concentration of protein in microspheres and the concentration of protein in the incubation medium were determined using the method of Lowry et al. (O. H. Lowry et al., *J. Biol. Chem.*, 193: 265, 1951). The amount of alpha-1-PI released as function of time is presented in FIG. 2. FIG. 3 describes the cumulative release of alpha-1-PI from HES-polyacrylamide microspheres in $\mu$g of protein per mg of spheres. The incubation time is plotted in a square root scale. Characteristics of microspheres are those as in Table 2. Characteristics of the microspheres corresponds to those given in Example 5a–d.

While this invention has been described and illustrated with reference to certain preferred embodiments thereof, those skilled in the art will appreciate that various changes, modifications and substitutions can be made therein without departing from the spirit of the invention. It is intended, therefore, that the invention be limited only by the scope of the claims which follow.

What is claimed is:

1. A porous microsphere comprising a biodegradable polymeric structure having a three-dimensional polymeric network in which a biologically active macromolecular agent is physically entrapped therein and not substantially bonded to the polymeric network, said polymeric structure comprising a vinyl derivative of a biodegradable hydrophilic polymer copolymerized with a water-soluble monovinyl monomer, said macromolecular agent able to be released at a controlled rate by diffusion out of the pores and by degradation of the polymeric structure.

2. The porous microsphere according to claim 1, wherein said biodegradable hydrophilic polymer contains at least two vinyl groups or substituted vinyl groups per average polymer chain.

3. The porous microsphere of claim 2, wherein the vinyl derivative of the biodegradable hydrophilic polymer has the formula:

wherein $R_1$ represents a hydrogen atom or methyl group; n is 0, 1 or 2; X represents a radical having the formula:

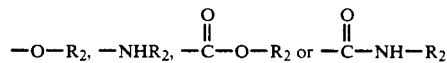

and wherein $R_2$ represents the biodegradable hydrophilic polymer which contains at least two vinyl or substituted vinyl groups per average polymer chain.

4. The porous microsphere according to claim 3, wherein the biodegradable hydrophilic polymer is selected from the group consisting of polysaccharides, proteinaceous polymers, soluble derivatives of polysaccharides, soluble derivatives of proteinaceous polymers, polypeptides, polyester and polyorthoesters.

5. The porous microsphere according to claim 4, wherein the biodegradable hydrophilic polymer is a polysaccharide.

6. The porous microsphere according to claim 5, wherein the polysaccharide is a starch derivative.

7. The porous microsphere according to claim 4, whereon the biodegradable hydrophilic polymer is a polypeptide.

8. The porous microsphere according to claim 7, wherein the polypeptide is poly-(N-hydroxyalkyl)asparagine or poly-(N-hydroxyalkyl)glutamine.

9. The porous microsphere according to claim 1, wherein the water-soluble monovinyl monomer is selected from the group consisting of hydrophilic esters and/or amides of acrylic or methacrylic acids, water-soluble vinyl derivatives, acrylic acid and methacrylic acid.

10. The porous microsphere according to claim 1, wherein the ratio between the biodegradable hydrophilic polymer to the water-soluble monovinyl monomer is in the range of about 1:5 to about 40:1 on a weight basis.

11. The porous microsphere according to claim 1, wherein the biologically active macromolecular agent is a hormone, protein, peptide, vaccine, enzyme or enzyme inhibitor.

12. The porous microsphere according to claim 11, whereon the biologically active macromolecular agent is a hormone.

13. The porous microsphere according to claim 1, wherein the biologically active macromolecular agent is a peptide.

* * * * *